(12) United States Patent
Ehr

(10) Patent No.: US 7,022,086 B2
(45) Date of Patent: Apr. 4, 2006

(54) GUIDEWIRE WITH ENCAPSULATED MARKER

(75) Inventor: Timothy G. J. Ehr, Elk River, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 113 days.

(21) Appl. No.: 10/152,435

(22) Filed: May 21, 2002

(65) Prior Publication Data

US 2004/0225231 A1    Nov. 11, 2004

(51) Int. Cl.
*A61B 5/00*    (2006.01)
*A61M 25/00*    (2006.01)

(52) U.S. Cl. ..................................... 600/585

(58) Field of Classification Search ............... 600/585, 600/433–435; 148/240; 428/375; 140/71 R; 264/259; 427/2.1, 2.12, 2.28, 372.2; 29/428, 29/592

See application file for complete search history.

(56) References Cited

U.S. PATENT DOCUMENTS

| | | | |
|---|---|---|---|
| 4,571,240 A | 2/1986 | Samson et al. | |
| 4,657,024 A | 4/1987 | Coneys | |
| 4,763,647 A | 8/1988 | Gambale | |
| 4,922,924 A | 5/1990 | Gambale et al. | |
| 5,063,935 A | 11/1991 | Gambale | |
| 5,144,959 A | 9/1992 | Gambale et al. | |
| 5,174,302 A | 12/1992 | Palmer | |
| 5,213,111 A | 5/1993 | Cook et al. | |
| 5,228,453 A | 7/1993 | Sepetka | |
| 5,241,970 A | 9/1993 | Johlin, Jr. et al. | |
| 5,253,653 A | 10/1993 | Daigle et al. | |
| 5,333,620 A | 8/1994 | Moutafis et al. | |
| 5,345,945 A | 9/1994 | Hodgson et al. | |
| 5,353,808 A | 10/1994 | Viera | |
| 5,368,048 A | 11/1994 | Stoy et al. | |
| 5,409,015 A | 4/1995 | Palermo | |
| 5,443,907 A | 8/1995 | Slaikeu et al. | |
| 5,452,726 A | 9/1995 | Burmeister et al. | |
| 5,562,127 A * | 10/1996 | Fanselow et al. | 138/137 |
| 5,606,981 A | 3/1997 | Tartacower et al. | |
| 5,636,642 A | 6/1997 | Palermo | |
| 5,772,609 A | 6/1998 | Nguyen et al. | |
| 5,797,857 A | 8/1998 | Obitsu | |
| 5,817,017 A | 10/1998 | Young et al. | |
| 5,833,631 A | 11/1998 | Nguyen | |
| 5,836,892 A | 11/1998 | Lorenzo | |
| 5,836,893 A | 11/1998 | Urick | |
| 5,876,356 A | 3/1999 | Viera et al. | |
| 5,916,178 A | 6/1999 | Noone et al. | |
| 5,954,672 A | 9/1999 | Schwager | |
| 5,993,424 A | 11/1999 | Lorenzo et al. | |
| 5,997,487 A | 12/1999 | Kolehmaineu et al. | |
| 6,027,461 A | 2/2000 | Walker et al. | |
| 6,139,510 A | 10/2000 | Palermo | |
| 6,171,295 B1 | 1/2001 | Garabedian et al. | |

(Continued)

FOREIGN PATENT DOCUMENTS

| | | |
|---|---|---|
| EP | 0 407 965 | 1/1991 |
| EP | 0 868 925 A2 | 7/1998 |
| JP | 07275367 A * | 10/1995 |
| JP | 9-94298 | 8/1997 |
| WO | WO 91/00051 | 1/1991 |
| WO | WO 01/95794 A1 | 12/2001 |

*Primary Examiner*—Charles Marmor
(74) *Attorney, Agent, or Firm*—Crompton, Seager & Tufte LLC

(57) ABSTRACT

A guidewire having a marker member and method of manufacturing the same. In some embodiments, the invention includes a marker member disposed around the longitudinal axis of an elongate shaft and embedded within an outer sheath.

1 Claim, 4 Drawing Sheets

U.S. PATENT DOCUMENTS

| | | |
|---|---|---|
| 6,183,420 B1 | 2/2001 | Douk et al. |
| 6,251,086 B1 | 6/2001 | Cornelius et al. |
| 6,306,105 B1 | 10/2001 | Rooney et al. |
| 6,494,847 B1 * | 12/2002 | Richardson et al. ........ 600/585 |
| 6,620,114 B1 * | 9/2003 | Vrba et al. .................. 600/585 |
| 6,636,758 B1 * | 10/2003 | Sanchez et al. ............. 600/434 |
| 6,673,025 B1 * | 1/2004 | Richardson et al. ........ 600/585 |
| 2002/0042582 A1 | 4/2002 | Vrba et al. |
| 2003/0069521 A1 * | 4/2003 | Reynolds et al. ............ 600/585 |
| 2003/0120181 A1 * | 6/2003 | Toma et al. ................. 600/585 |

* cited by examiner

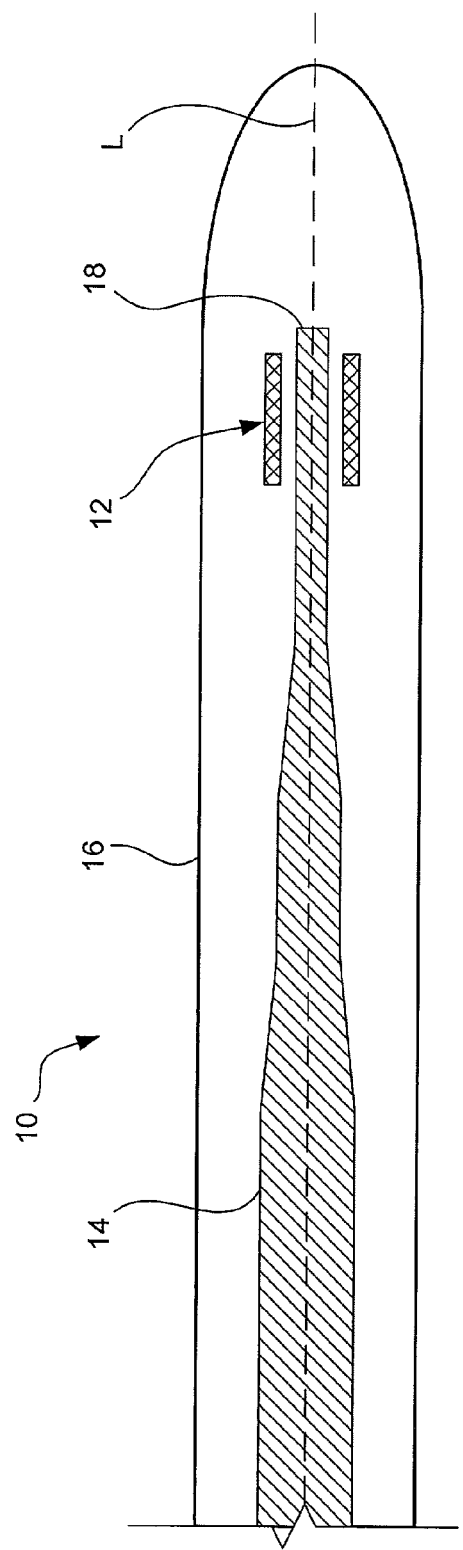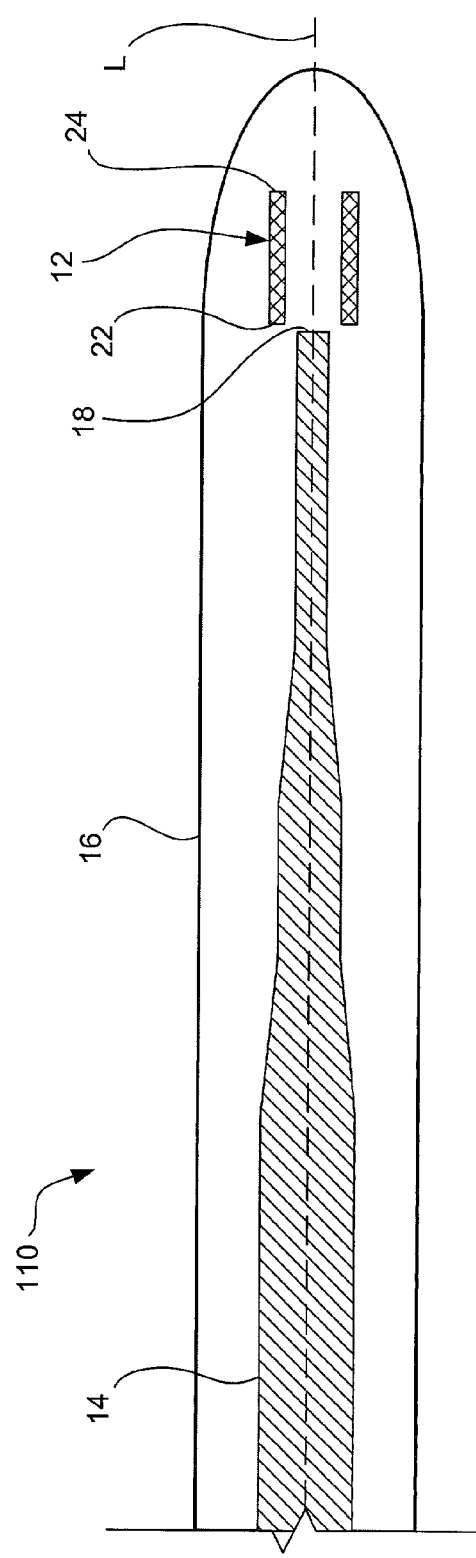

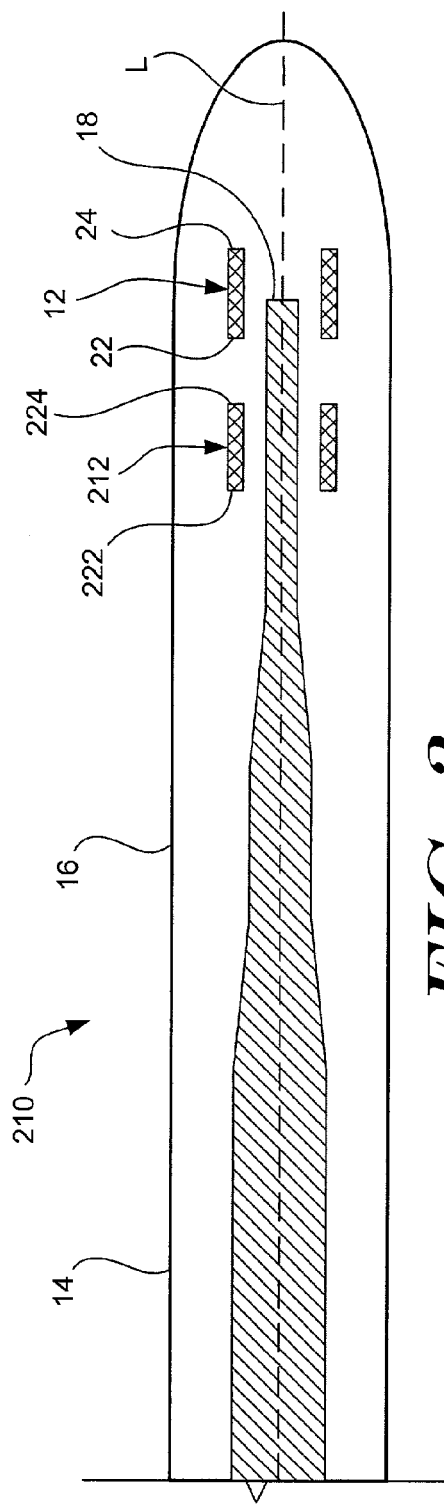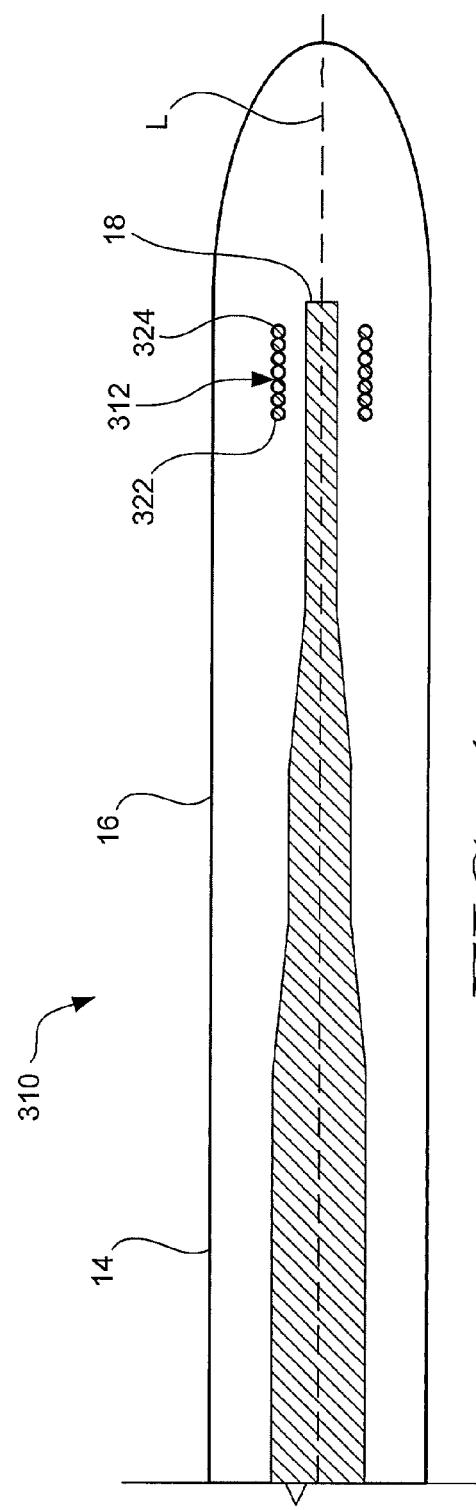

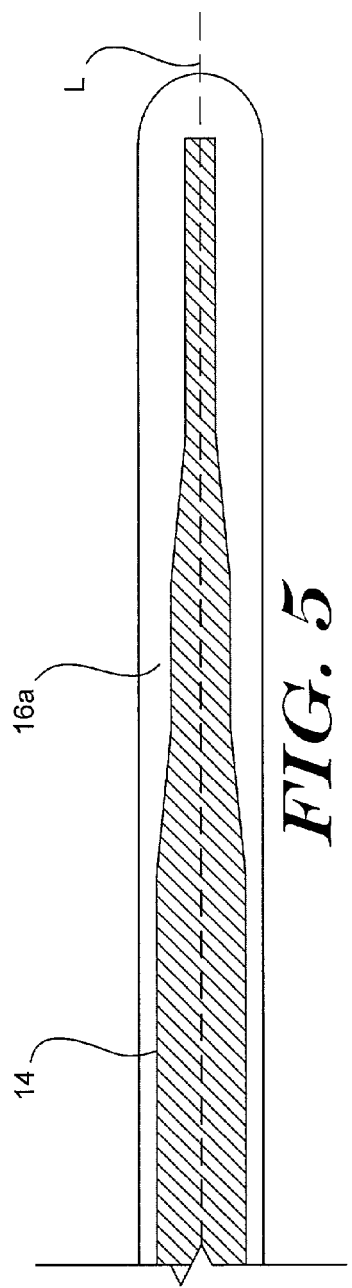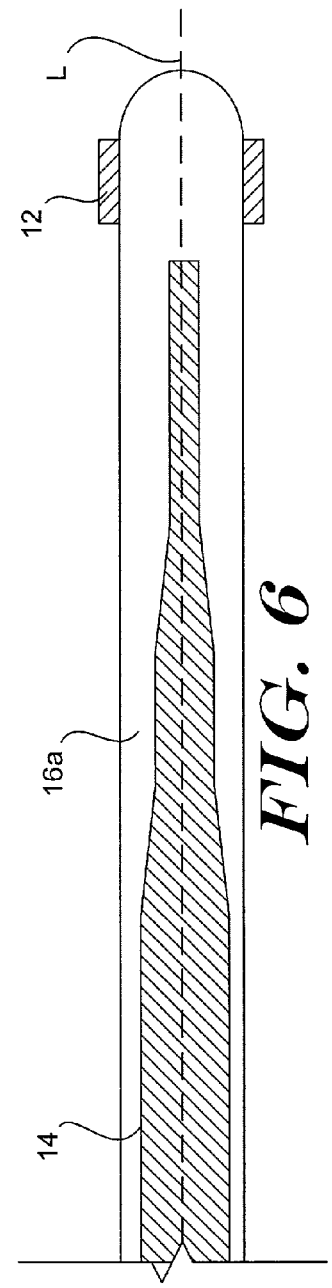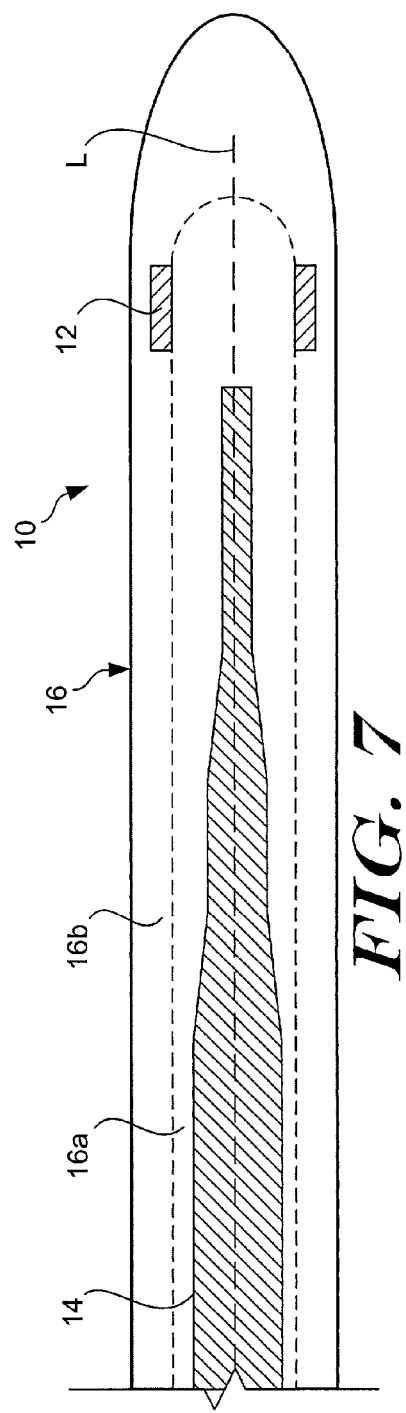

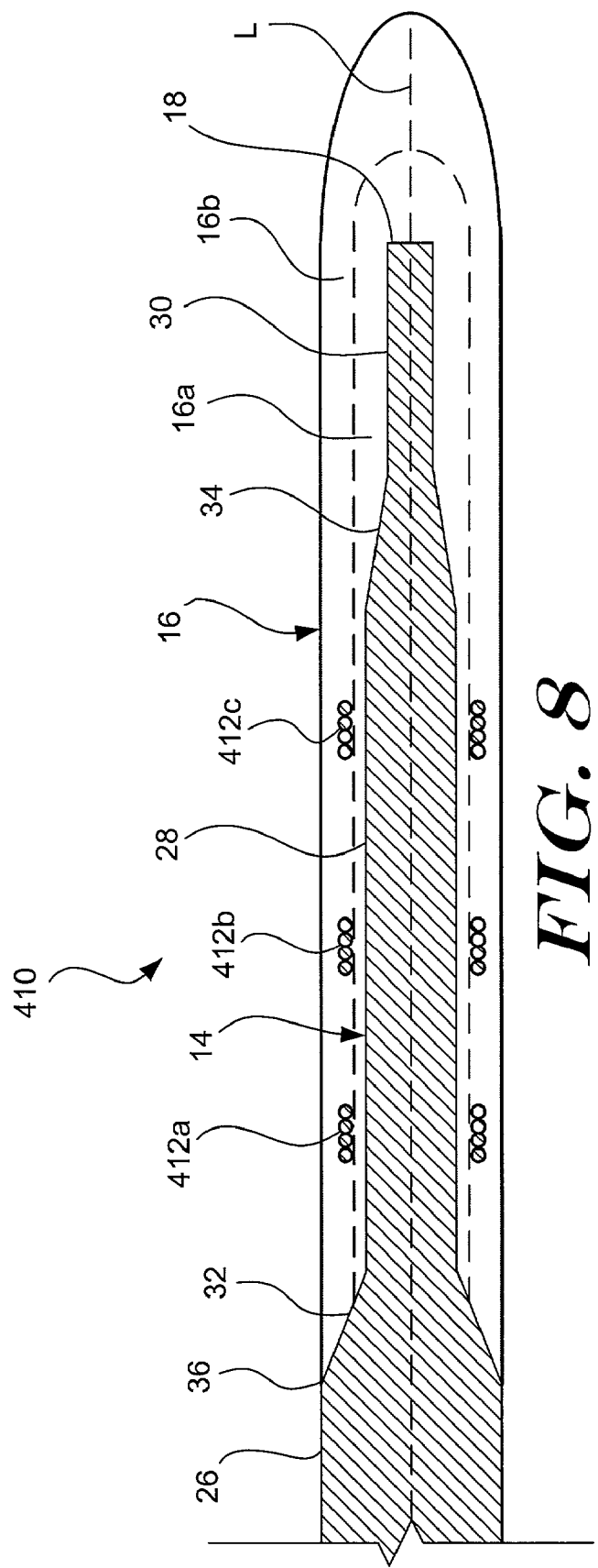

GUIDEWIRE WITH ENCAPSULATED MARKER

FIELD OF THE INVENTION

The invention pertains to guidewires and, more particularly, to guidewires having a structure incorporated therein that is adapted and configured to produce a relatively bright image on a fluoroscopy screen or another imaging technique.

BACKGROUND

A wide variety of guidewires have been developed for medical use, for example, intravascular use. Some of these guidewires have a radiopaque marker attached to them. The radiopaque marker can be used to monitor the location of the guidewire. Of the known guidewires that have a radiopaque marker, each has certain advantages and disadvantages. There is an ongoing need to provide alternative guidewire structures and assemblies.

SUMMARY

The invention provides design, material, and manufacturing method alternatives for guidewires having a marker. In some embodiments, a marker member is disposed around the longitudinal axis of an elongate shaft and encapsulated within an outer sheath.

BRIEF DESCRIPTION OF THE DRAWINGS

FIG. 1 is a cross-sectional view of an embodiment of an elongate guidewire having a marker member encapsulated within an outer sheath;

FIG. 2 is a cross-sectional view of another embodiment of an elongate guidewire having a marker member encapsulated within an outer sheath;

FIG. 3 is a cross-sectional view of another embodiment of an elongate guidewire having multiple marker members encapsulated within an outer sheath;

FIG. 4 is a cross-sectional view of another embodiment of an elongate guidewire having a marker member encapsulated within an outer sheath;

FIG. 5 is a cross-sectional view of a first sheath layer disposed over an elongate shaft;

FIG. 6 is a cross-sectional view of a marker member disposed over the first sheath layer shown in FIG. 5;

FIG. 7 is a cross-sectional view of second sheath layer disposed over the marker member, first sheath layer, and shaft shown in FIG. 6; and FIG. 8 is a cross-sectional view of another embodiment of an elongate guidewire having multiple marker members encapsulated within an outer sheath.

DETAILED DESCRIPTION

The following description should be read with reference to the drawings wherein like reference numerals indicate like elements throughout the several views. The detailed description and drawings illustrate example embodiments of the claimed invention.

Many guidewire designs have a radiopaque marker member such as a band or coil attached to a shaft to help a user monitor the location of the guidewire. The invention, in at least some embodiments, includes a guidewire having one or more marker members embedded within an outer sheath. Other embodiments relate to methods of making such guidewires. In at least some embodiments, the embedding of the marker member within the sheath is the sole attachment mechanism for attaching the marker to the guidewire. Some of the features described herein and some of the example embodiments shown in FIGS. 1-8 can incorporate or provide desirable properties. For example, in some embodiments, embedding a marker member within the sheath allows the guidewire to have a smooth, lubricious exterior surface and the lubricous exterior surface can allow the guidewire to slide more freely within, for example, a catheter lumen. Other desirable properties of some embodiments may include, but are not limited to, elimination of the need of an adhesive, solder, or braze to attach the marker member to a central shaft; the ability to extend the marker member distally beyond a distal end of the shaft; and the ability to alter the radiopacity and stiffness/flexibility characteristics of the guidewire.

FIG. 1 is a cross-sectional view of an example embodiment of an elongate guidewire 10 having a marker member 12 disposed around the longitudinal axis L of an elongate shaft 14 and encapsulated within an outer sheath 16. For illustration purposes only, FIGS. 1–7 depict guidewire 10 (and analogous guidewires) as an intravascular guidewire. However, it can be appreciated that in other embodiments, guidewire 10 could also be another type of guidewire, for example, an endoscopic device, an arthroscopic device, and the like.

Shaft 14 includes a proximal end (not shown), a distal end 18, and can be made of any material suitable including metals, metal alloys, polymers, or the like, or combinations or mixtures thereof. Some examples of suitable metals and metal alloys include stainless steel, such as 304 v stainless steel; nickel-titanium alloy, such as nitinol, nickel-chromium alloy, nickel-chromium-iron alloy, cobalt alloy, or the like; or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

The entire shaft 14 can be made of the same material, or in some embodiments, can include portions or sections made of different materials. In some embodiments, the material used to construct shaft 14 is chosen to impart varying flexibility and stiffness characteristics to different portions of shaft 14. For example, a proximal portion and a distal portion of shaft 14 may be formed of different materials (i.e., materials having different moduli of elasticity) resulting in a difference in flexibility. In some embodiments, the material used to construct the proximal portion can be relatively stiff for pushability and torqueability, and the material used to construct the distal portion can be relatively flexible by comparison for better lateral trackability and steerability. For example, the proximal portion can be formed of straightened 304v stainless steel wire, and the distal portion can be formed of a straightened super elastic or linear elastic alloy (e.g., nickel-titanium) wire.

In embodiments where different portions of shaft 14 are made of different material, the different portions are connected using any suitable connecting techniques. For example, the different portions of the core wire can be connected using welding, soldering, brazing, adhesive, or the like, or combinations thereof. Additionally, some embodiments can include one or more mechanical connectors or connector assemblies to connect the different portions of the core wire that are made of different materials. The connector may comprise any structure generally suitable for connecting portions of a guidewire. One example of a suitable structure includes a structure such as a hypotube or a coiled wire which has an inside diameter sized appropriately to receive and connect to the ends of the proximal portion and the distal portion. Other examples of suitable techniques and structures that can be used to interconnect different shaft sections are disclosed in U.S. patent application Ser. No. 09/972,276, which is incorporated herein by reference.

Shaft 14 can have a solid cross-section as shown, but in some embodiments, can have a hollow cross-section. In yet other embodiments, shaft 14 can include a combination of areas having solid cross-sections and hollow cross sections. Shaft 14 can be continuously tapered, can have a tapered section or a number or series of tapered sections of differing diameters, or can have a constant diameter. In some embodiments, shaft 14 is tapered or otherwise formed to have a geometry that decreases in cross sectional area toward distal end 18. If tapered, shaft 14 can include a uniform or a non-uniform transition of the sections, depending on the transition characteristics desired. For example, shaft 14 may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

Shaft 14 may be tapered or shaped by any one of a number of different techniques, for example, by centerless grinding methods. The centerless grinding technique may utilize an indexing system employing sensors (e.g., opticaVreflective, magnetic) to avoid excessive grinding of the connection. In addition, the centerless grinding technique may utilize a CBN or diamond abrasive grinding wheel that is well shaped and dressed to avoid grabbing shaft 14 during the grinding process. In some embodiments, shaft 14 is centerless ground using a Royal Master HI-AC centerless grinder.

The length of shaft 14 (or the length of individual portions thereof) are typically dictated by the length and flexibility characteristics desired in the final guidewire. For example, shaft 14 may include a proximal portion having a length in the range of about 20 to about 300 centimeters and a distal portion having a length in the range of about 3 to about 50 centimeters. It can be appreciated that alterations in the length of shaft 14 or portions thereof can be altered without departing from the spirit of the invention.

Marker member 12 is disposed around longitudinal axis L of shaft 14. Longitudinal axis L of shaft 14 is understood to be an axis running along the length of shaft 14. Longitudinal axis L of shaft 14 is understood to extend beyond distal end 18 and the proximal end of shaft 14, following the same general path or direction as shaft 14. The location of marker member 12 can be described relative to longitudinal axis L of shaft 14. For example, describing marker member 12 as being disposed around longitudinal axis L of shaft 14 can include marker member 12 being disposed around shaft 14. Additionally, being disposed around longitudinal axis L of shaft 14 can also include marker member 12 being disposed at a location distal to distal end 18 of shaft 14.

In some embodiments, marker member 12 includes radiopaque materials. Radiopaque materials are understood to be materials capable of producing a relatively bright image on a fluoroscopy screen or another imaging technique during a medical procedure. This relatively bright image aids the user of guidewire 10 in determining its location. Radiopaque materials can include, but are not limited to, gold, platinum, palladium, tantalum, tungsten alloy, plastic material loaded with a radiopaque filler, and the like.

The structure of marker member 12 can include any shape or form suitable for encapsulation within sheath 16. For example, in some embodiments marker member 12 may comprise a tubular, partially tubular, cylindrical (i.e., "C" or "U" shaped), a straight or cupped structure, or other suitably shaped member that is disposed adjacent longitudinal axis L of shaft 14. The marker member 12 can have a generally constant diameter configuration, or in some embodiments can be tapered, for example, to correspond with a taper of the core. Such a tapered marker can also provide variable radiopacity in some embodiments. Because marker member 12 is embedded within outer sheath 16, it can be seen that marker member 12 is spaced from shaft 14. In the embodiment of FIG. 1, marker member 12 may comprise a generally tubular shaped structure, such as a marker band.

From FIG. 1, it can be seen that marker member 12 need not be directly attached to shaft 14. In some embodiments, this may be desirable because a solder or adhesive joint (or other suitable connection) between shaft 14 and marker member 12 may create a relatively rigid or inflexible zone within guidewire 10. Moreover, because it is often desirable to place markers (e.g., marker member 12) near the distal end of guidewire 10, and because it is often desirable for the distal end of such guidewires to be highly flexible, eliminating the need for a solder joint may allow for greater distal flexibility. FIGS. 2–8 illustrate alterative example embodiments of guidewire 10, where the location, number, and type of marker member 12 is altered. These alternative embodiments are discussed in more detail below.

As stated above, marker member 12 may be embedded within sheath 16. By "embedded" it is meant that marker member 12 is completely encapsulated, surrounded, or covered on all sides by sheath 16.

Sheath 16 may be made of, for example, a polymer such as a thermoplastic or thermosetting polymer. For example, sheath 16 may be made of polyurethane, polyether-ester (for example a polyether-ester elastomer such as ARNITEL® available from DSM Engineering Plastics), polyester (for example a polyester elastomer such as HYTREL® available from DuPont), or linear low-density polyethylene (for example REXELL®), and the like, or copolymers or mixtures or combinations thereof. Additionally, sheath 16 may be made of polymers such as polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, and the like, or mixtures, combinations, or copolymers thereof, or with any of the other materials listed above. Polyamides, for example, are particularly suitable for providing a relatively rigid sheath 16. Some other suitable materials for a rigid tubular member include polyetheretherketone (PEEK), polyimide (PI), and polyetherimide (PEI). PEBA, in contrast to the rigid polyamides, is a relatively flexible polymeric material. The use of a polyamide can impart a slightly less rigid durometer than the rigid polyamides and slightly greater than the flexible PEBA material. In some embodiments, sheath 16 may be a single polymer, multiple layers, or a blend of polymers. In some embodiments sheath 16 can include a liquid crystal polymer (LCP) blended with other polymers to enhance torqueability. By employing careful selection of materials and processing techniques, thermoplastic, solvent soluble, and thermosetting variants of these and other materials can be employed to achieve the desired results. In some embodiments the sheath can be relatively clear material while in other embodiments the sheath can be more opaque or colored, depending upon the desired visual characteristics.

Additionally, in some embodiments, a coating, for example a lubricious (e.g., hydrophylic) or other type of coating may be applied over portions or all of sheath 16, and/or other portions of guidewire 10. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of guidewire 10 is coated with a hydrophilic polymer as discussed above, and the more proximal portion is coated with a fluoropolymer, such as polytetrafluroethylene (PTFE).

FIG. 2 is a cross-sectional view of an alternative embodiment of a guidewire 110. Guidewire 110 is similar in structure to guidewire 10 shown in FIG. 1, except that the position of marker member 12 has been altered relative to shaft 14. As shown in FIG. 2, marker member 12 includes a proximal end 22 and a distal end 24 and proximal end 22 is positioned distally of distal end 18 of shaft 14. Altering the position of marker member 12 relative to shaft 14 may incorporate desirable properties into guidewire 110. For example, it may be desirable to distally truncate shaft 14 in order to give guidewire 110 a more flexible distal tip. Because marker member 12 can be positioned beyond distal end 18 of shaft 14, the distal tip can still easily be imaged (beyond distal end 18 of shaft 14) by monitoring the location of marker member 12.

In general, marker member 12 is positioned near distal end 18 of shaft 14. However, it can be appreciated that marker member 12 could be positioned at essentially any position along the length of guidewire 110.

FIG. 3 is a cross-sectional view of a guidewire 210, which is similar in structure to the guidewire 10 shown in FIG. 1, but illustrates some other positions of marker member 12 along longitudinal axis L of shaft 14. For example, marker member 12 may be positioned such that proximal end 22 is located proximally of distal end 18 of shaft 14, and distal end 24 is located distally of distal end 18 of shaft 14. From FIG. 3 it can also be appreciated that guidewire 210 can also include one or more additional marker members 212. Marker member 212 could also be positioned at essentially any position along the length of guidewire 110. For example, marker member 212 may be positioned so that proximal end 222 and distal end 224 are located proximally of distal end 18 of shaft 14. Alternatively, marker member 212 could be positioned distally of shaft 14 (as shown in FIG. 2), partially overlapping with distal end 18 of shaft 14 (similar to marker member 12 of FIG. 3).

FIG. 4 is a cross-sectional view of a guidewire 310. Guidewire 310 is similar in structure to guidewire 10 as shown in FIG. 1, except that the marker member 312 having proximal end 322 and distal end 324 is a coil, for example a tubular coil. In some embodiments, coil 312 includes radiopaque material, and may be completely made of, partially made of, or plated with a radiopaque material. Thus, marker member 312 may be used to aid a user in monitoring the position of guidewire 310, for example, within the human body.

Coil 312 may be arranged or configured in essentially any suitable matter. For example, the number of coils, pitch between windings of the coil, thickness of coil wire, shape of coil wire, and other structural parameters can be altered without departing from the spirit of the invention. Moreover, marker member 312 may be positioned essentially anywhere along longitudinal axis L of shaft 14, including locations distal of distal end 18 of shaft 14 similar to marker member 12 in FIG. 2. Thus, marker member 312 may be positioned similar to marker member 12 in FIG. 1, 2, or 3, for example, or at any other suitable location.

Encapsulation of coil marker member 312 can provide additional advantages. For example, in some embodiments, the encapsulation of coil 312 can reduce or eliminate coil bunching or override, which can cause damage to the coil or wire, or can cause wire lockup, for example, within a catheter. Additionally, the coil geometry and configuration can be varied to provide for variable flexibility and radiopacity characteristics. For example, the diameter of the coil, the pitch of the coil, the thickness of the wire and other like structural aspects of the coil can be varied along the length to provide for variable characteristics.

FIGS. 5–7 illustrate an embodiment of a method of manufacturing guidewire 10 (or any of the guidewires described herein). FIG. 5 is a cross-sectional view of a first sheath layer 16a disposed over shaft 14 which has been ground to provide a tapered shape. In some embodiments, sheath layer 16a is a portion of outer sheath 16 that is disposed over shaft 14. Layer 16a may be disposed over shaft 14 using any one of a number of manufacturing techniques. For example, layer 16a may be disposed over shaft 14 by extrusion, molding, casting, thermal forming, thermal-reforming (such as infrared heat flow or reflow techniques), and other suitable techniques.

After disposing layer 16a over shaft 14, additional processing may occur. For example, layer 16a may be ground, worked, or finished to give it an appropriate size, diameter, and/or texture. In some embodiments it may be useful for layer 16a to have a generally smooth exterior surface to allow other objects (e.g., marker member 12) to be tightly attached thereto. Alternatively, it may be beneficial to have some degree of "roughness" or unevenness to layer 16a. In some embodiments, this may aid in maintaining the marker positions during processing, or may aid in the blending of layer 16a with other layers.

Marker member 12 may be disposed over layer 16a in another manufacturing step as illustrated in FIG. 6. Again, it can be appreciated that marker member 12 can be disposed at essentially any location along layer 16a as discussed above. Moreover, additional marker members 12 can be disposed along layer 16a and marker member 12 can comprise a band, coil, or other suitable structure as described above.

In some embodiments, it may be desirable, but not essential, to attach or couple the marker member 12 to layer 16a using suitable attachment techniques, for example adhesives, thermal bonding, laser bonding, crimping, and the like. In some embodiments, thermal bonding may be advantageous because it may eliminate any need to include adhesives or other attachment mechanisms that could impact the flexibility of guidewire 10. Alternatively, adhesives (for example, ultraviolet adhesives, thixon, and the like), mechanical attachment, or other attachment techniques could be used. Some examples of suitable adhesives include materials similar to or compatible with the material of layer 16a. Additional processing or manufacturing steps may then take place wherein the marker member 12 and/or layer 16a are ground, worked, or finished.

A second sheath layer 16b can then be disposed over first layer 16a and marker member 12, as shown in FIG. 7. Second layer 16b may be disposed over layer 16a and marker member 12 using a suitable technique, for example by extruding, molding, casting, thermal forming, thermal-reforming (e.g., I/R heat flow or reflow), or any other suitable method. In addition, the second layer 16b can be worked, ground, finished, and the like to give guidewire 10 the desired exterior texture and/or shape. Because layer 16b may comprise the outermost layer of guidewire 10, it may be desirable in some embodiments to provide the exterior of layer 16b with a smooth surface. However, alternative textures may be appropriate in other embodiments.

In some embodiments, manufacturing guidewire 10 may also include the blending of layer 16b with layer 16a. This may include thermal processing of guidewire 10 that can result in partial melting or another suitable physical change of layers 16a/16b so that the layers flow together or join to form a seamless single layer (i.e., outer sheath 16). According to this embodiment, the boundary between layers 16a/16b would essentially be eliminated and only a single structure, sheath 16, would remain.

It can be appreciated that the blending of layers 16a and 16b could be described in any one of a number of different ways. For example, the step of blending layer 16a with layer 16b may be described as melting together, coupling, reflowing the layers, encapsulating, embedding, and the like. It can also be appreciated that blending of layers 16a/16b can occur without adding an additional step. For example, manufacturing may take place at a relatively rapid rate so that layer 16a is still partially molten or warm when layer 16b is disposed over layer 16a and marker member 12, such that the two layers blend together without additional manufacturing steps. None-the-less, the result of the blending of layers 16a/16b is the formation of sheath 16 as shown in FIG. 1–4 and 7.

In some embodiments, when the two layers of material are connected together, a pocket or void can be maintained about the site of the marker member. Some such embodiments can improve flexibility of the structure. For example, if the maker is a coil, the coil can flex feely within the pocket.

In some embodiments, layers 16a and 16b may be made of the same material (e.g., polyurethane). This may allow the blending of layers 16a/16b to result in a truly seamless joining to form sheath 16. Alternatively, layers 16a/16b may be made of different, but compatible, materials that also could be essentially seamlessly joined.

In some alterative embodiments, the layers 16a/16b for example, are not necessarily blending together to form a seamless joint, but rather are maintained in position relative to one another using suitable bonding techniques, for example, adhesives, mechanical bonding, and the like.

In some embodiments, guidewire 10 (or any of the guidewires described herein) may include additional structure or manufacturing steps. For example, guidewire 10 may include a support structure disposed under, within, or around sheath 16. The support member may comprise a coil, braid, additional polymeric layer, or other structure, and may extend along a portion or the complete length of guidewire 10.

FIG. 8 is a cross-sectional view of a guidewire 410, which is similar to guidewire 10 as shown in FIG. 1, but illustrates three sets of marker members 412a/b/c (shown as coils), and that the sheath 16 may cover only a portion of shaft 14. It will be understood by those of skill in the art and others that a broad variety of materials, dimensions, and structures can be used to construct suitable embodiments (including all those describe above), depending upon the desired characteristics. The following examples of some dimensions for guidewire 410 are included by way of example only, and are not intended to be limiting.

In some specific embodiments, guidewire 410 has the general structure set fourth in FIG. 8 and may be manufactured according to any of the methods described above. Shaft 14 may also include a first constant diameter portion 26, a second constant diameter portion 28, and a third constant diameter portion 30. Between portion 26 and portion 28 can be a first tapered portion 32, and between portion 28 and portion 30 can be a second tapered portion 34.

The lengths of portions 26/28/30 may be in the range of about 20 to 150 inches for portion 26, for example, about 37.5 inches; about 1 to 5 inches for portion 28, for example, about 2.5 inches; and about 0.5 to 2.5 inches for portion 30, for example, about 1 inch. The portions 26/28/30 may also have outside diameters in the range of about 0.01 to about 0.02, for example about 0.013 inches, for portion 26; about 0.002 to about 0.006, for example about 0.0044 inches, for portion 28; and about 0.001 to about 0.004, for example about 0.003 inches, for portion 30.

Tapered portions 32/34 may taper at a constant angle, a varying angle, a curvilinear fashion, a stepwise fashion, or in any other suitable manner. First tapered portion 32 may be in the range of about 0.1 to about 0.5 inches in length, for example about 0.3 inches, and second tapered portion 34 may be in the range of about 0.5 to about 3 inches in length, for example about 1 inch.

As shown in FIG. 8, marker members 412a/b/c can be disposed around second portion 28 (i.e., over first layer 16a). It can be appreciated, however, that marker 110 members 412 could be disposed at essentially any position along longitudinal axis L of shaft 14 as described above. For example, marker member 412a may be disposed about 2 to 5 inches, for example about 3.9 inches, from distal end 18 of shaft 14. Similarly, marker member 412b may be disposed about 1.5 to 4.5 inches, for example about 3.2 inches, from distal end 18 of shaft 14, and marker member 412c may be disposed about 1 to 4 inches, for example about 2.5 inches, from distal end 18 of shaft 14. In some examples, the spacing between any two marker members may be in the range of about 0.5 to 1.5 inches, for example about 0.7 inches.

In some embodiments, manufacturing guidewire 410 may include disposing first layer 16a over shaft 14 as shown in FIG. 5. In some embodiments, the outside diameter of layer 16a may be in the range of about 0.004 to about 0.010 inches, for example about 0.0062 inches. Moreover, the outside diameter of second layer 16b (and, therefore, sheath 16) may be in the range of about 0.01 to about 0.02, for example about 0.013 inches. As shown in FIG. 8, sheath 16 covers first taper 32, second portion 28, second taper 34, and third portion 30 of shaft 14. In some embodiments, a proximal end 36 of sheath 16 may extend up to first portion 26 of shaft 14. This will provide a generally constant outside diameter for guidewire 410 from portion 26 to sheath 16.

Thus, sheath 16 can have an outside diameter that is about equal to the outside diameter of portion 26.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of manufacturing a guidewire, comprising:
   providing an elongate core wire having a proximal end and a distal end;
   disposing a first polymeric layer over at least a portion of the core wire;
   disposing a marker member around at least a portion of the first polymeric layer, wherein a distal end of the marker member is disposed distally of the distal end of the core wire and a proximal end of the marker member is disposed proximally of the distal end of the core wire;
   disposing a, second polymeric layer over the first polymeric layer and the marker, and
   blending the first polymeric layer and the second polymeric layer to form a seamlessly joined single layer that encapsulates the marker member.

* * * * *

UNITED STATES PATENT AND TRADEMARK OFFICE
CERTIFICATE OF CORRECTION

| | |
|---|---|
| PATENT NO. | : 7,022,086 B2 |
| APPLICATION NO. | : 10/152435 |
| DATED | : April 4, 2006 |
| INVENTOR(S) | : Timothy G.J. Ehr |

Page 1 of 1

It is certified that error appears in the above-identified patent and that said Letters Patent is hereby corrected as shown below:

<u>Column 3,</u>
Line 33, delete "opticaVreflective" and insert -- optical/reflective --.

<u>Column 10,</u>
Line 7, delete the coma ",".
Line 8, delete the coma "," and insert the semi-colon -- ; --.

Signed and Sealed this

Eleventh Day of July, 2006

JON W. DUDAS
*Director of the United States Patent and Trademark Office*